(12) United States Patent
Chuang et al.

(10) Patent No.: US 11,029,319 B2
(45) Date of Patent: Jun. 8, 2021

(54) BIOSENSOR AND APPLICATION OF THE SAME

(71) Applicant: NATIONAL CHENG KUNG UNIVERSITY, Tainan (TW)

(72) Inventors: Han-Sheng Chuang, Tainan (TW); Ching-Chuen Chen, New Taipei (TW); Yu-Ting Tseng, Taichung (TW)

(73) Assignee: NATIONAL CHENG KUNG UNIVERSITY, Tainan (TW)

( * ) Notice: Subject to any disclaimer, the term of this patent is extended or adjusted under 35 U.S.C. 154(b) by 275 days.

(21) Appl. No.: 16/157,094

(22) Filed: Oct. 11, 2018

(65) Prior Publication Data

US 2020/0116734 A1    Apr. 16, 2020

(51) Int. Cl.

| | |
|---|---|
| *G01N 33/68* | (2006.01) |
| *G02C 7/04* | (2006.01) |
| *G02C 11/00* | (2006.01) |
| *G01N 21/64* | (2006.01) |
| *A61B 5/1455* | (2006.01) |
| *A61B 10/00* | (2006.01) |
| *A61B 5/00* | (2006.01) |
| *A61B 5/145* | (2006.01) |

(52) U.S. Cl.
CPC ....... *G01N 33/6893* (2013.01); *A61B 5/1455* (2013.01); *A61B 5/14507* (2013.01); *A61B 5/6821* (2013.01); *A61B 10/0045* (2013.01); *G01N 21/64* (2013.01); *G02C 7/04* (2013.01); *G02C 11/10* (2013.01); *A61B 2010/0067* (2013.01); *G01N 2333/47* (2013.01); *G01N 2800/164* (2013.01)

(58) Field of Classification Search
None
See application file for complete search history.

(56) References Cited

U.S. PATENT DOCUMENTS

| | | | | |
|---|---|---|---|---|
| 2002/0049389 | A1* | 4/2002 | Abreu | A61B 5/412 600/558 |
| 2014/0088381 | A1* | 3/2014 | Etzkorn | A61B 5/14507 600/309 |
| 2016/0223842 | A1* | 8/2016 | Yun | G02C 7/04 |
| 2017/0020442 | A1* | 1/2017 | Flitsch | A61B 5/6802 |
| 2017/0024771 | A1* | 1/2017 | Flitsch | A61B 5/6821 |
| 2017/0042480 | A1* | 2/2017 | Gandhi | A61B 5/0015 |
| 2017/0119311 | A1* | 5/2017 | Iwasaki | A61H 23/02 |
| 2017/0181669 | A1* | 6/2017 | Lin | A61B 5/145 |

FOREIGN PATENT DOCUMENTS

| | | |
|---|---|---|
| CN | 104126121 A | 10/2014 |
| CN | 102576021 B | 4/2015 |

OTHER PUBLICATIONS

Joh, Daniel Y. et al., Inkjet-printed point-of-care immunoassay on a nanoscale polymer brush enables subpicomolar detection of analytes in blood, Aug. 2017, PNAS, E7054-E7062 (Year: 2017).*
Lee, Wang Sik et al., An Antibody-Immobilized Silica Inverse Opal Nanostructure for Label-Free Optical Biosensors, Jan. 2018, MDPI Sensors, 1-10 (Year: 2018).*
Vasquez, Yolanda et al., Three-Phase Co-assembly: In Situ Incorporation of Nanoparticles into Tunable, Highly Ordered, Porous Silica Films, Nov. 2013, ACS Photonics, 53-60 (Year: 2013).*
Elsherif, Mohamed et al., Wearable Contact Lens Biosensors for Continuous Glucose Monitoring Using Smartphones, May 2018, ACS NANO, 5452-5462 (Year: 2018).*
Chen, Yihao et al., Skin-like biosensor system via electrochemical channels for noninvasive blood glucose monitoring, Dec. 2017, Science Advances, pp. 1-7 (Year: 2017).*

* cited by examiner

*Primary Examiner* — Ann Y Lam
(74) *Attorney, Agent, or Firm* — CKC & Partners Co., LLC

(57) ABSTRACT

The present invention provides a biosensor and an application of the same. The biosensor includes a substrate, a first polymer layer and a second polymer layer. The first polymer layer includes composite antibodies, each of which includes a first antibody and a labelling molecule. The second polymer layer has an inverse opal photonic crystal structure where gold nanoparticles and second antibodies are distributed. At least one of the composite antibodies, an antigen and at least one of the second antibodies forms a complex in the second polymer layer, and an antigen concentration is obtained by a fluorescence intensity, a degree of red-shift or a change in a visual color of the biosensor.

8 Claims, 22 Drawing Sheets

BIOSENSOR AND APPLICATION OF THE SAME

BACKGROUND

Field of Invention

The present invention relates to a biosensor and an application thereof. More particularly, the present invention relates to a biosensor including a photonic crystal structure, and a method of detecting an antigen concentration by using the biosensor.

Description of Related Art

A common method for detecting diabetic retinopathy is ocular optical coherence tomography (OCT) or fluorescence angiography. However, these apparatuses are expensive, and detecting methods using the apparatuses are invasive. In addition, the detecting methods using the apparatuses have disadvantages such as time-consuming, difficult to diagnose an early symptom, and limited sampling.

It is known that lipocalin 1 (LCN1) may be a biomarker of diabetic retinopathy. Generally, a concentration of LCN1 in tear of a normal person is about 1 to 2 mg/ml, while a concentration of LCN1 in tear of a patient of diabetic retinopathy may be several times compared to the normal value. Therefore, diabetic retinopathy may be diagnosed by a variation in the concentration of LCN1. However, the variation in the concentration is minor, and how to detect this minor variation is one of the problems required to be overcome.

An inverse opal photonic structure is often used to enhance an optical property (e.g. a fluorescence intensity) of detection, and a change in its structure leads to a change of refraction and reflection. Accordingly, the variation in the analyte concentration may be detected by a change in the reflection peak.

A method is provided to observe changes in glucose, pH and potassium ion concentration by arranging hydrogel beads capable of detecting the glucose, the pH and the potassium ion concentration on a contact lens. Changes of the wavelength range and visual color in the method results from a change in the distance between bead to bead due to swelling or shrinkage of the hydrogel beads. However, the changes of the wavelength range and the visual color are not significant in a low analyte concentration. Moreover, this method is unable to detect proteins.

Another method is provided, in which different antibodies are respectively attached to photonic crystal hydrogel films having different codes, and the different antibodies that correspond to different analytes. The respective reflection peaks of the photonic crystal hydrogel films having different codes are then detected. Next, the analytes are reacted with the antibodies and attached to the photonic crystal hydrogel films, followed by detecting the reflection peaks again. As a result of the antibody-analyte complex forming on the photonic crystal hydrogel film, the reflection peak will shift. This method is applicable to detect proteins while the limitation of the low analyte concentration cannot be overcome.

A further method is provided, which is similar to the method of attaching antibodies to the film. However, in this method, a secondary antibody is further added after the reaction of the analytes and the antibody, so as to increase the degree of refraction of the photonic crystal. Nevertheless, operations of the method are complicated, and the increased degree of refraction still cannot overcome the limitation of the low analyte concentration.

In view of the disadvantages, a biosensor and a method of detecting an antigen concentration are required, so as to detect a low antigen concentration with high sensitivity. Furthermore, uniform sampling and a long-term examination of the variation in the antigen concentration are realized by the biosensor and the method.

SUMMARY

Therefore, one aspect of the invention provides a biosensor which can efficiently increase the fluorescence intensity and a degree of redshift, thereby detecting an antigen at low concentrations, and/or directly determining an antigen concentration according to a change of the visual color of the biosensor.

Another aspect of the present invention provides a method of detecting an antigen concentration, and the method is performed by using the biosensor.

According to the aspect of the present invention, a biosensor is provided first. In some embodiments, the biosensor includes a substrate, a first polymer layer and a second polymer layer. The substrate includes a first region and a second region adjoined to the first region, and the second region is located on one side of the first region. The first polymer layer is disposed in the first region. Plural composite antibodies are distributed in the first polymer layer, and each of the composite antibodies includes a labelling molecule and a first antibody connected to the labelling molecule. The second polymer layer is disposed in the second region. The second polymer layer has an inverse opal photonic crystal structure, and the inverse opal photonic crystal structure comprises plural holes. Plural gold nanoparticles and plural second antibodies are disposed on a wall of each of the holes, and the first antibody and the second antibodies recognize the same antigen.

According to some embodiments of the present invention, the second region is located over the first region.

According to some embodiments of the present invention, a center of the substrate is concentrically surrounded by the first region and the second region in order from outside to inside.

According to some embodiments of the present invention, a bottom of the first region has a recessed cross section, and the recessed cross section has a first depth. In addition, a bottom of the second region has a recessed cross section having an asymmetric U-shape, the recessed cross section having the asymmetric U-shape has a second depth, and the second depth is greater than the first depth.

According to some embodiments of the present invention, the inverse opal photonic crystal structure is an inverted structure of a face-centered cubic structure of nanobeads, each of the nanobeads has a particle size in a range from 100 nm to 1000 nm, and the gold nanoparticles are distributed on a surface of each of the nanobeads.

According to some embodiments of the present invention, the labelling molecule includes a fluorescent molecule, and a particle size of each of the gold nanoparticles is in a range from 5 nm to 80 nm.

According to some embodiments of the present invention, the biosensor further includes a third polymer layer over the first polymer layer.

According to some embodiments of the present invention, the biosensor is a contact lens. The center of the substrate is an optical zone of the contact lens. The first region and the second region are located in a non-optical zone of the contact lens. The second polymer layer is exposed on one surface of the contact lens, and opposes the surface that is in direct contact with an eye.

According to the aspect of the present invention, a method of detecting an antigen concentration is provided. First, a biosensor described above is provided, in which a substrate of the biosensor includes a first region and a second region, where the second region is connected to the first region, and the second region is located on one side of the first region. A biological liquid sample containing an antigen flows from the second region to the first region of the biosensor, thereby releasing at least one of plural composite antibodies including a first antibody and a labelling molecule. At least one of the composite antibodies is allowed to react for a period of time with the antigen and at least one of plural second antibodies to form a complex in the second region. Next, an optical property of the complex in the second region of the biosensor is detected by a light source having a specific wavelength, in which the optical property includes a fluorescence intensity or a visual color. The antigen concentration is then obtained according to the optical property.

According to some embodiments of the present invention, the specific wavelength is in a range from 200 nm to 700 nm, and the fluorescence intensity is increased by at least two times based on an inverse opal photonic crystal structure in the second region.

BRIEF DESCRIPTION OF THE DRAWINGS

The invention can be more fully understood by reading the following detailed description of the embodiment, with reference made to the accompanying drawings as follows.

DETAILED DESCRIPTION

A purpose of the present invention provides a biosensor capable of detecting an antigen concentration. A composite antibody, an antigen and an antibody forms an immunosandwich structure in a polymer layer having an inverse opal photonic crystal structure where gold nanoparticles are distributed, such that an optical property (e.g. a fluorescence intensity or a degree of red-shift) of the biosensor is improved. The biosensor is applicable to detect the antigen at low concentrations, or obtain a variation in the antigen concentration according to a change in the visual color of the biosensor. In addition, uniform sampling and a long-term examination of the variation in the antigen concentration are realized by the biosensor. Furthermore, the biosensor is an optical device that does not require a driving device.

Figure 1A:
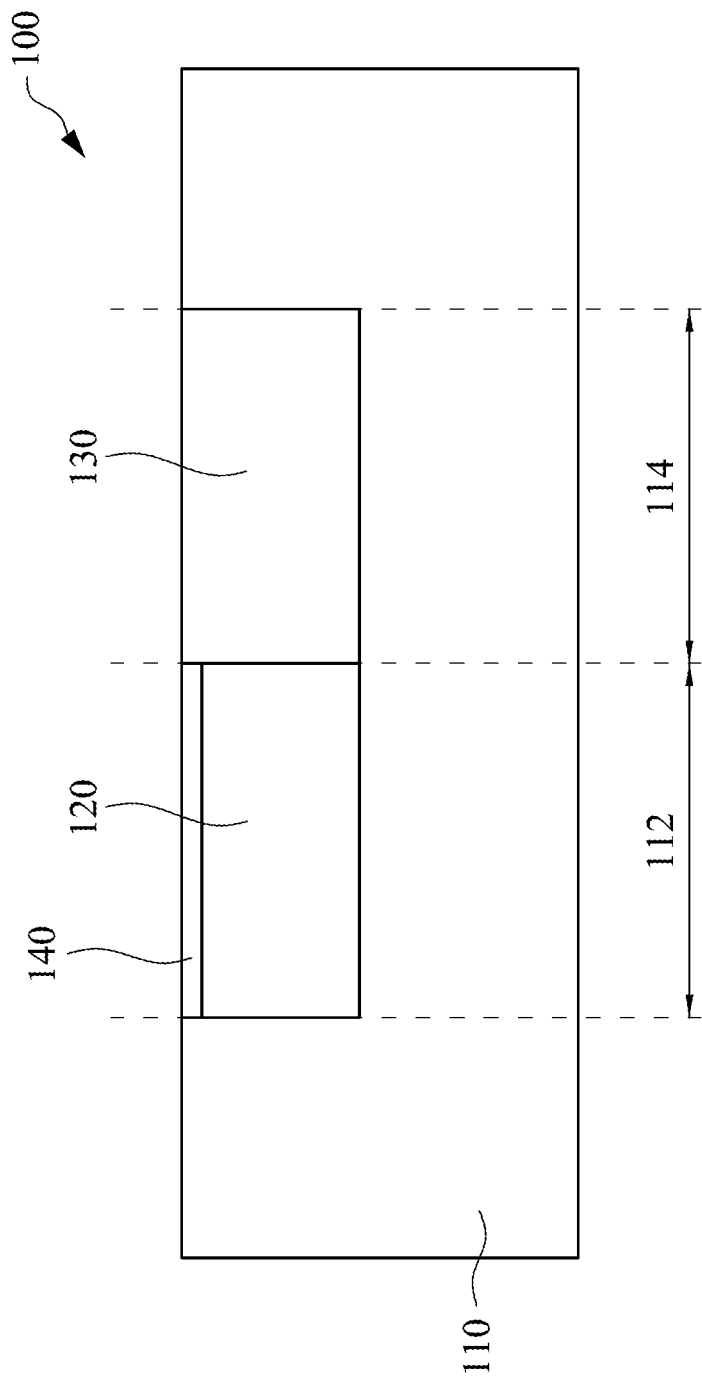
FIG. 1A is a cross sectional view of a biosensor in accordance with an embodiment of the present invention.

First, refer to FIG. 1A, FIG. 1A is a cross sectional view of a biosensor in accordance with an embodiment of the present invention. As shown in FIG. 1A, the biosensor 100 includes a substrate 110, a first polymer layer 120 and a second polymer layer 130. The substrate 110 includes a first region 112 and a second region 114 adjoined to the first region 112. The second region 114 is located on one side of the first region 112. The first polymer layer 120 is disposed in the first region 112, and the second polymer layer 130 is disposed in the second region 114.

Figure 1B:
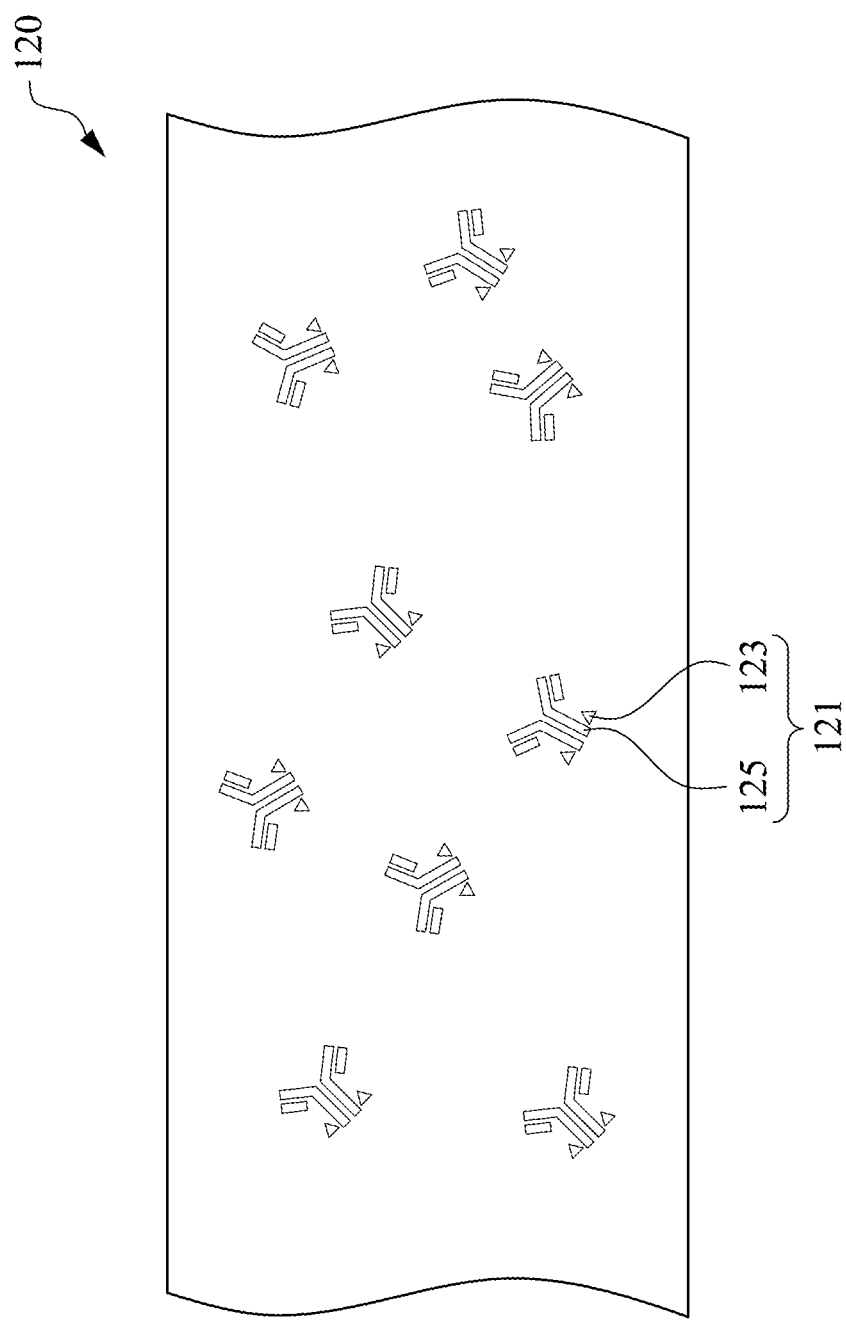
FIG. 1B is a schematic cross sectional view of a first polymer layer.

Next, please refer to FIG. 1B. FIG. 1B is a schematic cross sectional view of a first polymer layer. As shown in FIG. 1B, plural composite antibodies 121 are distributed in the first polymer layer 120. Each of the composite antibodies 121 includes a labelling molecule 123 and a first antibody 125 conjugated to the labelling molecule 123. In some embodiments, the first polymer layer 120 includes micropores (not shown), such that the composite antibodies 121 can flow into the second polymer layer 130 through the micropores. Each of the micropores may have an average pore size greater than 5 nm. Preferably, the average pore size of each of the micropores may be greater than 10 nm. In some embodiments, the labelling molecule 123 can include but is not limited to a fluorescent molecule. In one example, the fluorescent molecule may have an excitation wavelength in a range from 200 nm to 700 nm. In another example, the fluorescent molecule may have an emission wavelength in a range from 300 nm to 1000 nm. In a particular example, the fluorescent molecule can be coumarin, fluorescein, cyanine dye, tetramethylrhodamine ethyl ester perchlorate, P-phycoerythrin, phycocyanin, products having product names of Alexa Fluor 350, 405, 488, 532, 546, 555, 568, 594, 647, 680 or 750 (provided by Invitrogen), while the fluorescent molecule of the present invention is not limited to the examples.

Figure 1C:
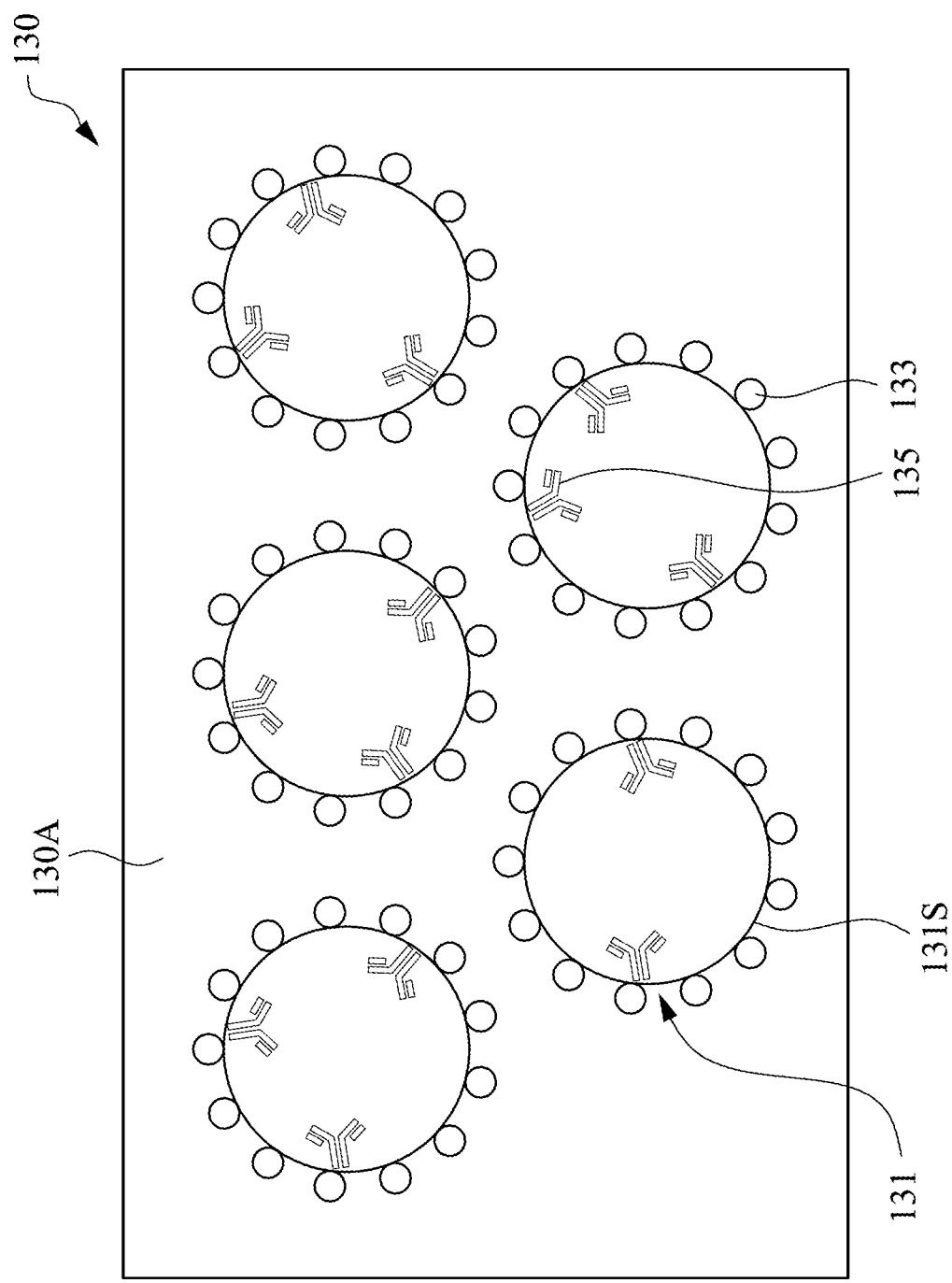
FIG. 1C is a cross sectional view of a second polymer layer.

FIG. 1C is a cross sectional view of a second polymer layer. As shown in FIG. 1C, the second polymer layer 130 has an inverse opal photonic crystal structure 130A, and the inverse opal photonic crystal structure 130A includes plural holes 131. Plural gold nanoparticles 133 and plural second antibodies 135 are disposed on a wall 131S of each of the holes 131. The second antibodies 135 and the first antibody 125 recognize the same antigen. For example, the first antibody 125 may be a polyclonal antibody of a specific antigen, and the second antibody 135 may be a monoclonal antibody of the specific antigen. In some embodiments, the second polymer layer 130 can also include the micropores as those of the first polymer layer 120. In some embodiments, a particle size of each of the gold nanoparticles 133 may be 5 nm to 80 nm. In some embodiments, the particle size of each of the gold nanoparticles 133 may be 40 nm. If the particle size of the gold nanoparticles 133 were too large, formation of the inverse opal photonic crystal structure would be affected, and a detecting property of the biosensor 100 could not be improved.

When the biosensor 100 is used to detect the antigen concentration, the composite antibodies 121 in the first polymer layer 120 and the second antibodies 135 in the second polymer layer 130 form the immuno-sandwich structure in the inverse opal photonic crystal structure 130A, thereby increasing a degree of refraction of light, and thus a fluorescence intensity and the degree of red-shift are improved. A surface plasma resonance occurs on surfaces of the gold nanoparticles 133 in the second polymer layer 130, thereby increasing the degree of reflection of light and further improving the fluorescence intensity of the labelling molecule 123. Moreover, when the antigen concentration is higher, the variation in the antigen concentration may be obtained by the change of the visual color of the biosensor 100.

Please refer to FIG. 1A again. In some embodiments, the biosensor 100 may further include a third polymer layer 140 over the first polymer layer 120. The third polymer layer 140 may include plural micropores (not shown), and each of the micropores has an average pore size not greater than 5 nm. The third polymer layer 140 can avoid leakage of the composite antibodies 121 from a top surface of the first polymer layer 120, thereby controlling a flow direction toward the second polymer layer 130 when the composite antibodies 121 contact a liquid sample.

In some embodiments, a material of the first polymer layer 120 and the second polymer layer 130 can include but is not limited to a hydrogel having the micropores with the average pore size greater than 5 nm. In some embodiments, the hydrogel may be poly alkylene glycol, polyacrylate or a copolymer including two or more poly alkylene glycol. In one specific example, the first polymer layer 120 may be polyhydroxyethylmethacrylate (pHEMA), Pluronic F-127, polyethylene glycol (PEG) or poly(ethylene glycol) diacrylate (PEGDA). In one specific example, the second polymer layer 130 may be PEG or PEGDA, so as to provide sufficient hardness for forming the inverse opal photonic crystal structure 130A. The hydrogel may be swelled after absorbing water, and thus the micropores are enlarged for the formation of the immuno-sandwich structure. In other embodiments, a material of the substrate 110 and the third polymer layer 140 may be polymethyl methacrylate (PMMA).

Figure 2:
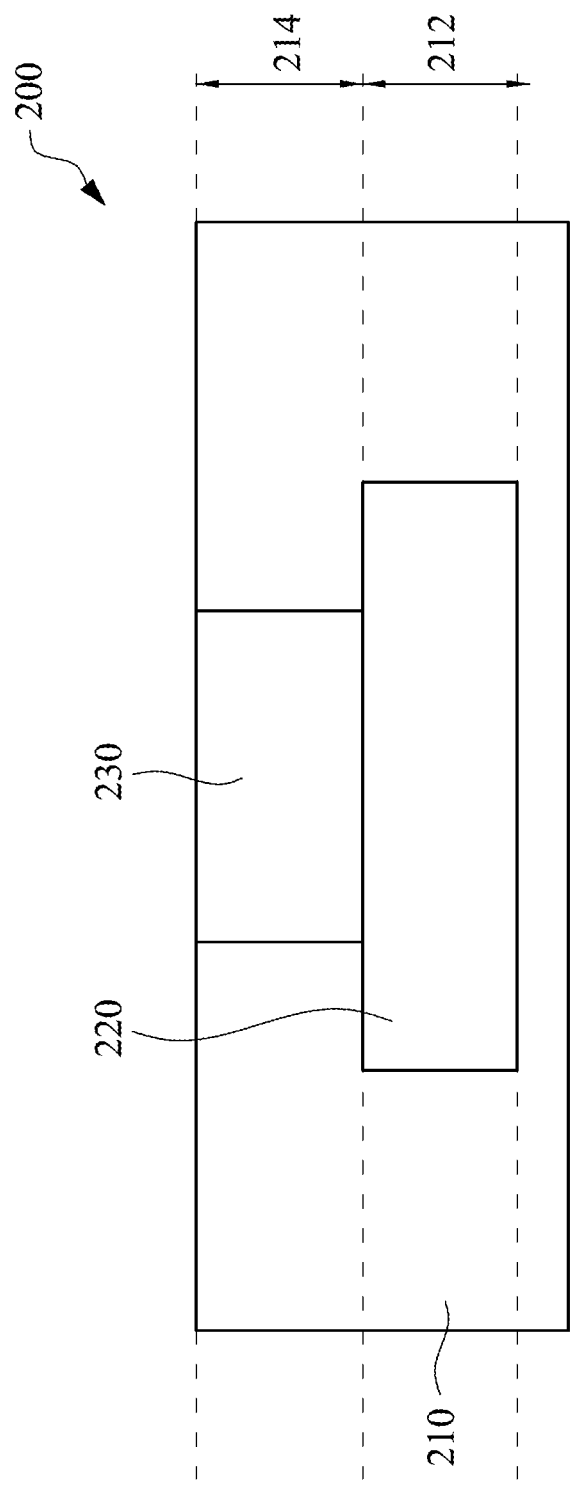
FIG. 2 is a cross sectional view of a biosensor in accordance with another embodiment of the present invention.

Next, please refer to FIG. 2. FIG. 2 is a cross sectional view of a biosensor in accordance with another embodiment of the present invention. As shown in FIG. 2, the biosensor 200 includes substrate 210, a first polymer layer 220 and a second polymer layer 230. The substrate 210 includes a first region 212 and a second region 214 adjoined to the first region 212. The second region 214 is located over the first region 212. The first polymer layer 220 is disposed in the first region 212, and the second polymer region 230 is disposed in the second region 214.

Figure 3A:
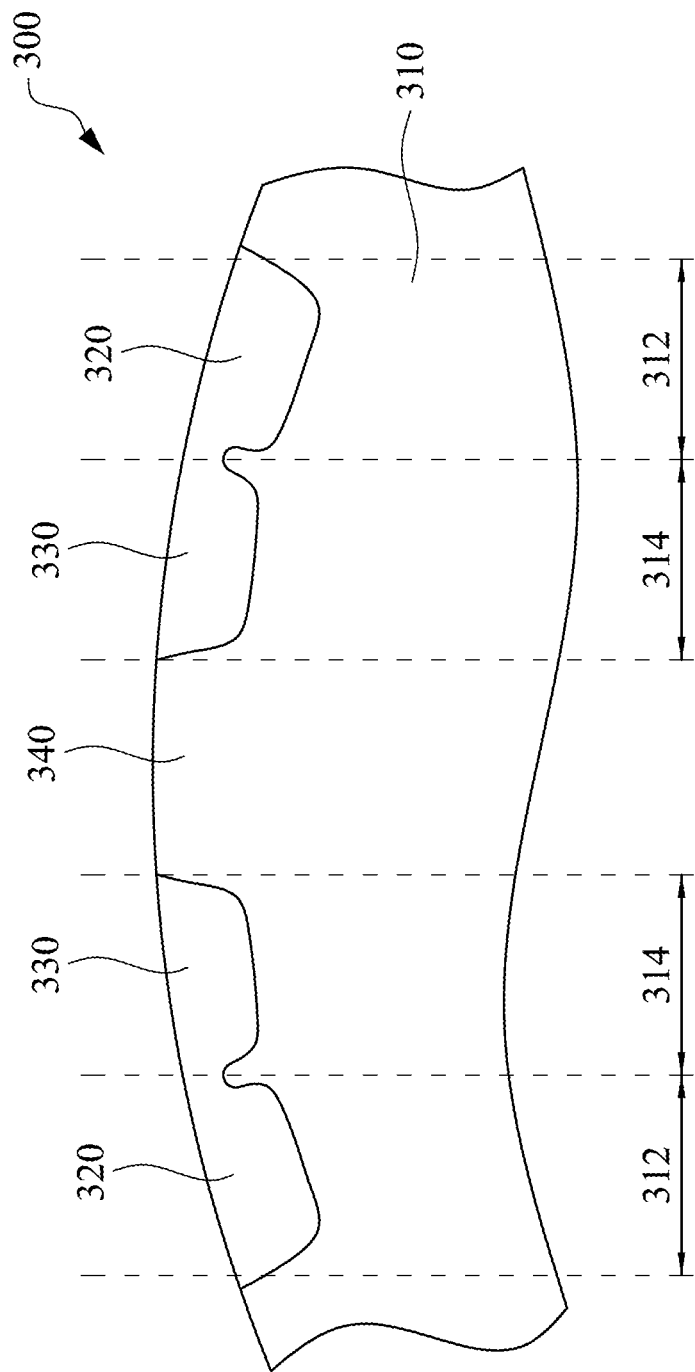
FIG. 3A and FIG. 3B are a cross sectional view and a top view of a biosensor in accordance with some embodiments of the present invention.
Figure 3B:
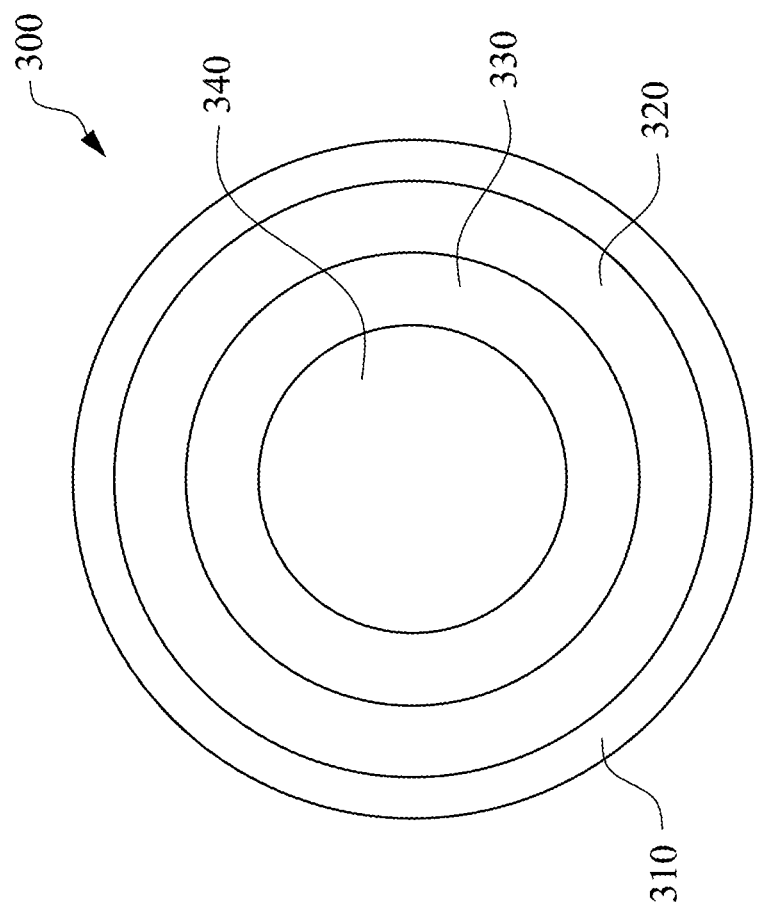

Please refer to FIG. 3A and FIG. 3B. FIG. 3A and FIG. 3B are respectively a cross sectional view and a top view of a biosensor in accordance with some embodiments of the present invention. In a biosensor 300, a center 340 of a substrate 310 is concentrically surrounded by a first region 312 and a second region 314 in order from outside to inside. The first region 312 and the second region 314 respectively form a ring-shaped region. A first polymer layer 320 and a second polymer layer 330 are respectively disposed on the ring-shaped first region 312 and the ring-shaped second region 314, thereby forming two concentric circles, as shown in FIG. 3B.

Figure 4:
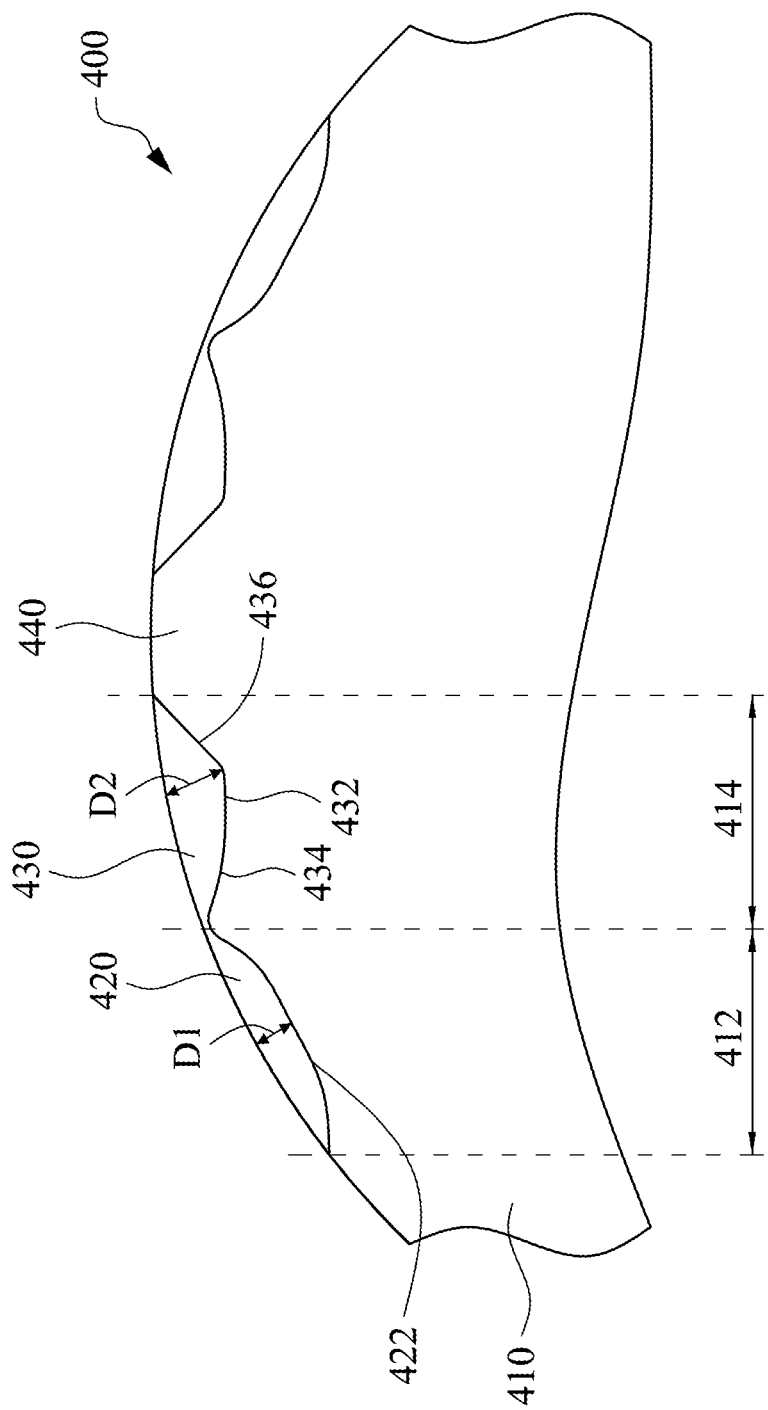
FIG. 4 is a cross sectional view of a biosensor in accordance with the other embodiments of the present invention.

FIG. 4 is a cross sectional view of a biosensor in accordance with the other embodiments of the present invention. In a biosensor 400, a substrate 410 includes a first region 412 and a second region 414. The first region 412 has a recessed cross section 422, and the recessed cross section 422 has a first depth D1. The second region 414 has a recessed cross section 432 having an asymmetric U-shape, the recessed cross section 432 having the asymmetric U-shape has a second depth D2. The second depth D2 is greater than the first depth D1.

In some embodiments, a slope of a side wall 436 of the recessed cross section 432 near a center 440, is greater than a slope of the other side wall 434 of the recessed cross section 432 near the first region 412. The configuration shown in FIG. 4 is beneficial for flow of the composite antibodies in a first polymer layer 420 flowing into a second polymer layer 430, and the optical property of the biosensor 400 is efficiently improved. The top view of FIG. 4 is similar to FIG. 3B, and may not be repeated herein.

Figure 5A:
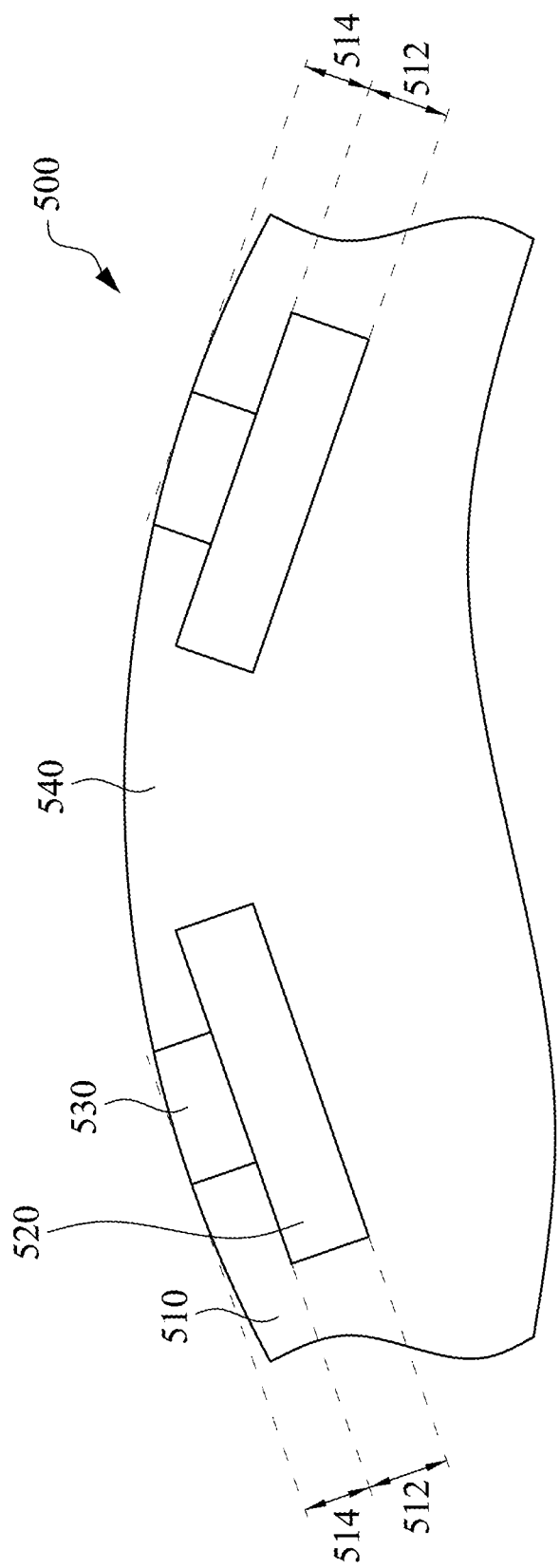
FIG. 5A and FIG. 5B are a cross sectional view and a top view of a biosensor in accordance with further embodiments of the present invention.
Figure 5B:
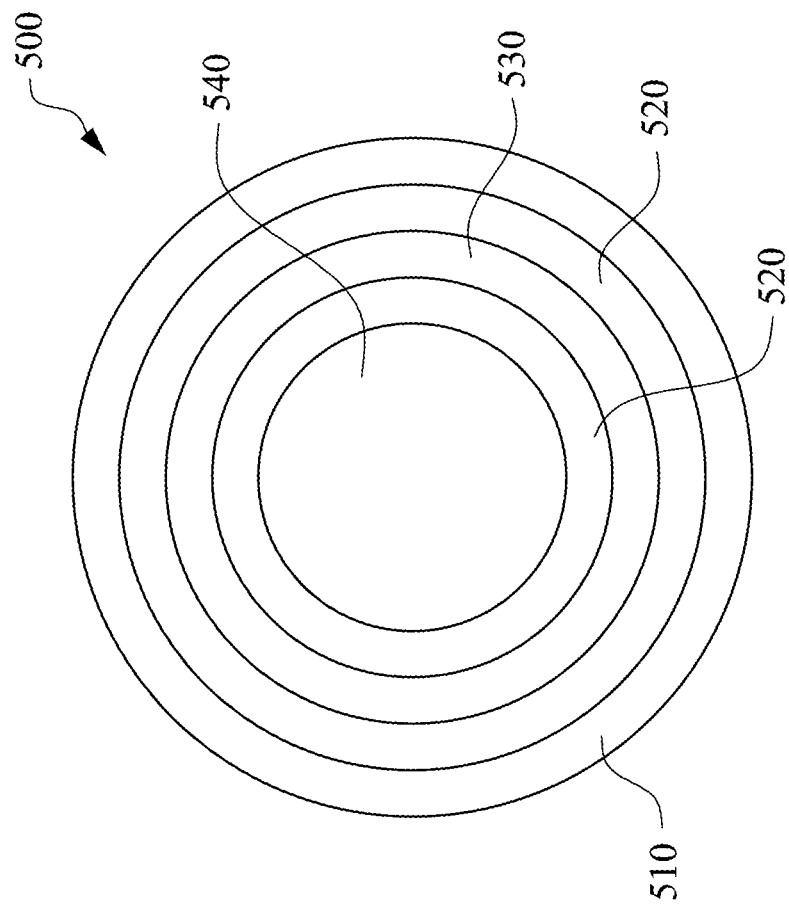

Please refer to FIG. 5A and FIG. 5B. FIG. 5A and FIG. 5B are respectively a cross sectional view and a top view of a biosensor in accordance with further embodiments of the present invention. In a biosensor 500, a second region 514 is located over a first region 512. As the biosensor 500 is viewed from the top view of FIG. 5B, a first polymer layer 520 and a second polymer layer 520 are two concentric circles that surround a center 540 of a substrate 510. However, what is different from FIG. 3B is that the second polymer layer 530 is located in the middle of the first polymer layer 520, such that the composite antibodies in the first polymer layer 520 may uniformly diffuse into the second polymer layer 530. A space of the first polymer layer 520 for storing the composite antibodies may be increased by the configuration of FIG. 5A and FIG. 5B. More composite antibodies improve the detecting property of the biosensor 500. For example, the fluorescence intensity to be detected may be increased.

In some embodiments, the biosensors 300, 400 and 500 may be contact lenses. The centers 340, 440 and 540 are an optical zone of the contact lens, and the first regions 312, 412 and 512 and the second regions 314, 414 and 514 are disposed in a non-optical zone of the contact lens. Furthermore, at least the second polymer layers 330, 430 and 530 are exposed on one surface of the contact lens, and opposes the surface that is in direct contact with an eye.

Figure 6A:
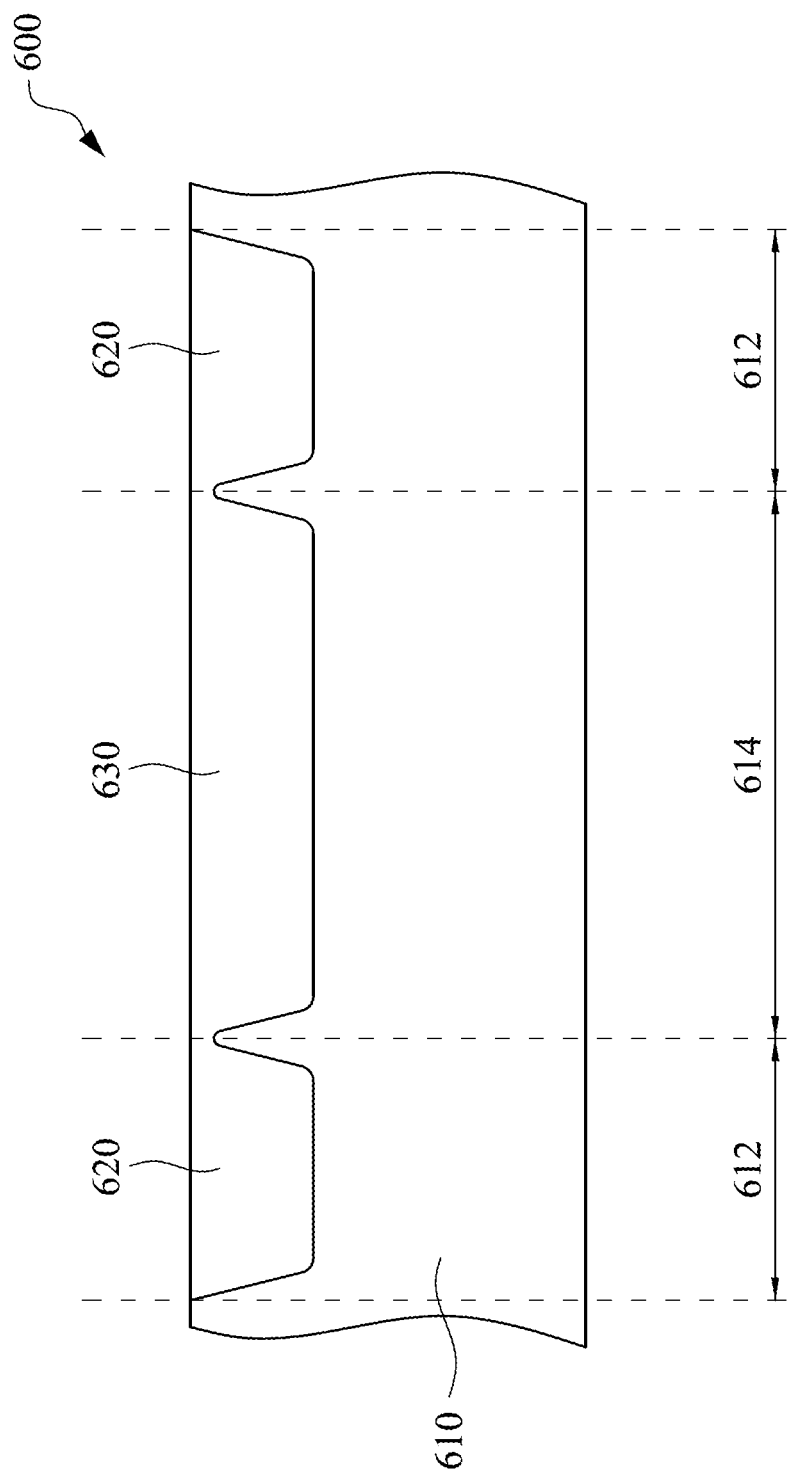
FIG. 6A and FIG. 6B are a cross sectional view and a top view of a biosensor in accordance with the other embodiments of the present invention.
Figure 6B:
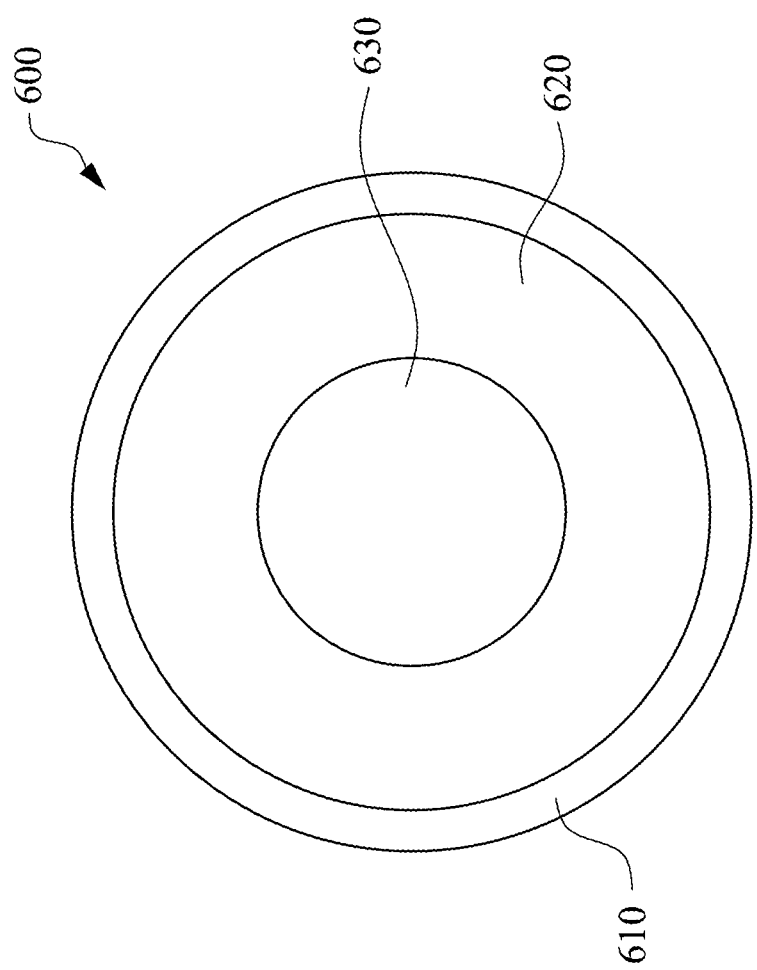

Please refer to FIG. 6A and FIG. 6B. FIG. 6A and FIG. 6B are a cross sectional view and a top view of a biosensor in accordance with the other embodiments of the present invention. As shown in FIG. 6A and FIG. 6B, a biosensor 600 includes a substrate 610, a first polymer layer 620 and a second polymer layer 630. A center of the substrate 610 is concentrically surrounded by a first region 612 and a second region 614 in order from outside to inside. The first polymer layer 620 and the second polymer layer 630 are respectively disposed on the first region 612 and the second region 614. The center (e.g. the optical zone of FIG. 5A and FIG. 5B) of the biosensor 600 is covered by the second polymer layer 630. In some embodiments, the biosensor 600 may be a detecting chip. One or more detecting chips may be arranged in a sample plate, so as to detect several samples or perform repeated experiments of a sample simultaneously.

The first polymer layers 220, 320, 420, 520 and 620 in FIG. 2 to FIG. 6B are same as the first polymer layer 120 shown in FIG. 1B. The second polymer layer 230, 330, 430, 530 and 630 are same as the second polymer layer 130, and may not be repeated herein.

The following description provides a method of producing the biosensor. The biosensor 100 is used as an example for simplification of figures. However, a person who has ordinary skills in the art can understand that the biosensors 200, 300, 400, 500 and 600 in FIG. 2 to FIG. 6B may be produced by a similar method.

The substrate 110 of the biosensor 100 is produced by a mould, in which the substrate 110 has the first region 112 and the second region 114 communicated to the first region 112, as shown in FIG. 1A. The mould may be produced by, for example, 3D printing. Next, the second polymer layer 130 is formed on the second region 114 first.

Figure 7A:
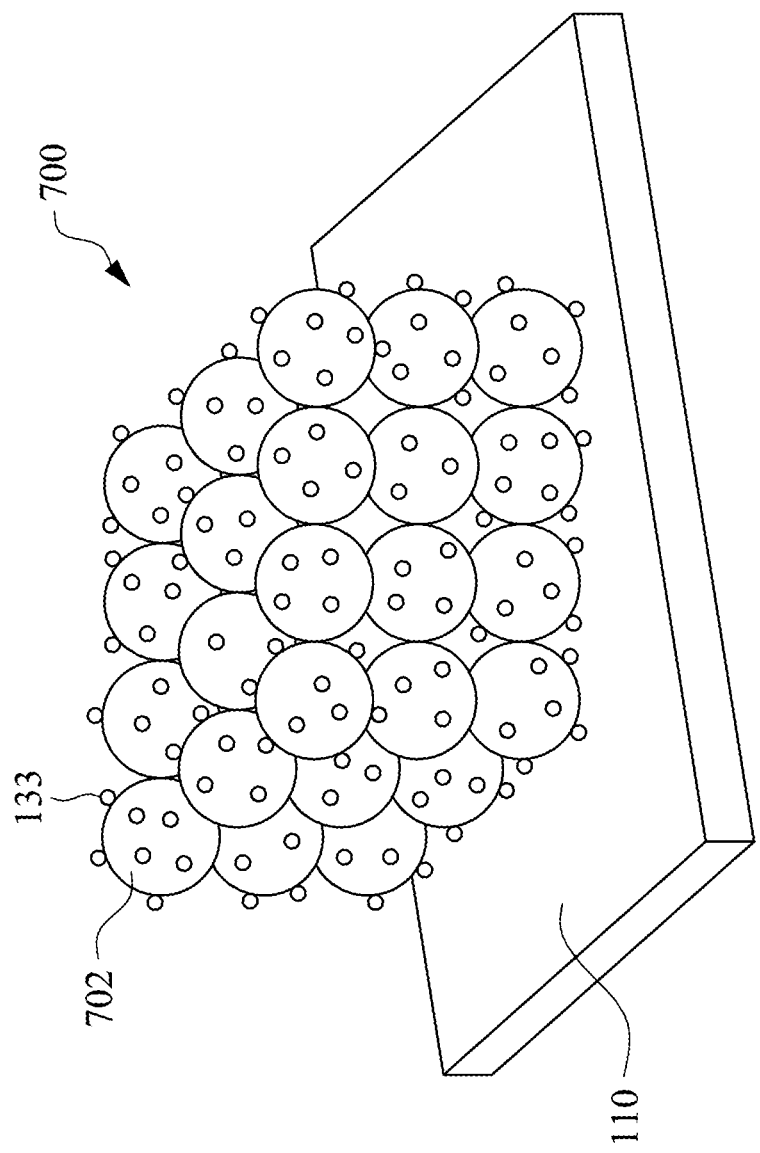
FIG. 7A through FIG. 7E are a method for forming a second polymer layer.

Please refer to FIG. 7A through FIG. 7E. FIG. 7A through FIG. 7E are a method for forming a second polymer layer. As shown in FIG. 7A, first, a nanobead mixture is applied to the second region 114 of the substrate 110, so as to form a three-dimensional structure of a face-centered cubic structure 700 by fluidic self-assembly. A planar substrate is illustrated instead of the region 114 for simplification of figures. The nanobead mixture includes silicon dioxide nanobeads 702 and gold nanoparticles 133 dispersed in a solution in some embodiments. When the face-centered cubic structure 700 is formed, the gold nanoparticles 133 are attached on surfaces of the silicon dioxide nanobeads 702. In one example, a particle size of each of the silicon dioxide nanobeads 702 is in a range from 100 nm to 1000 nm. For example, the particle size of each of the silicon dioxide nanobeads 702 may be 300 nm. In one embodiment, a weight ratio of the silicon dioxide nanobeads 702 and the gold nanoparticles 133 in the nanobead mixture is 10:1 to 30:1. If the amount of the gold nanoparticles were greater than the upper limit, the gold nanoparticles 133 may self-aggregate and the particle size of the gold nanoparticles 133 would be greater than a desired dimension. In other embodiments, the nanobeads may be formed from polymeric materials (e.g. polystyrene) or metallic materials, which may be etched by organic solvents or acidic/basic solutions.

Figure 7B:
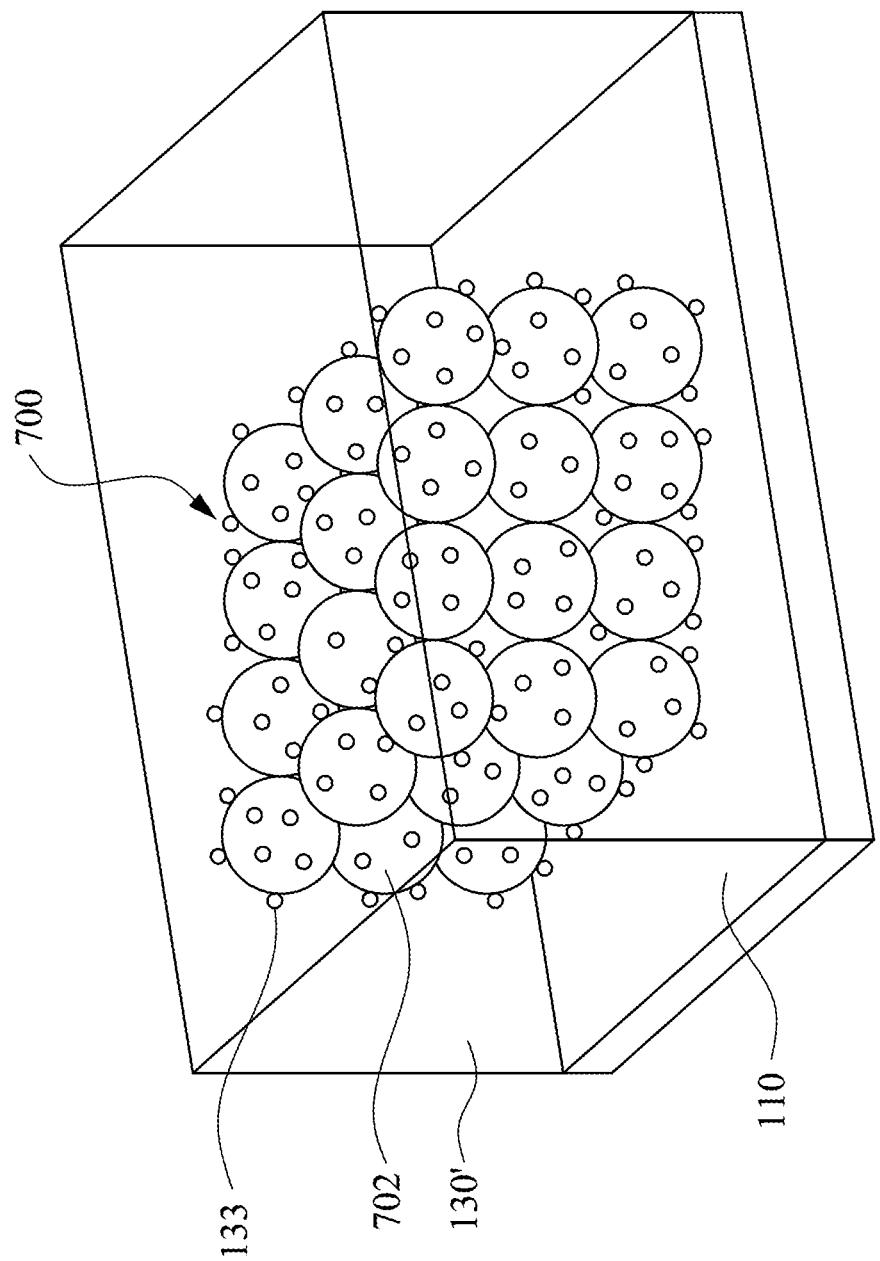
Figure 7C:
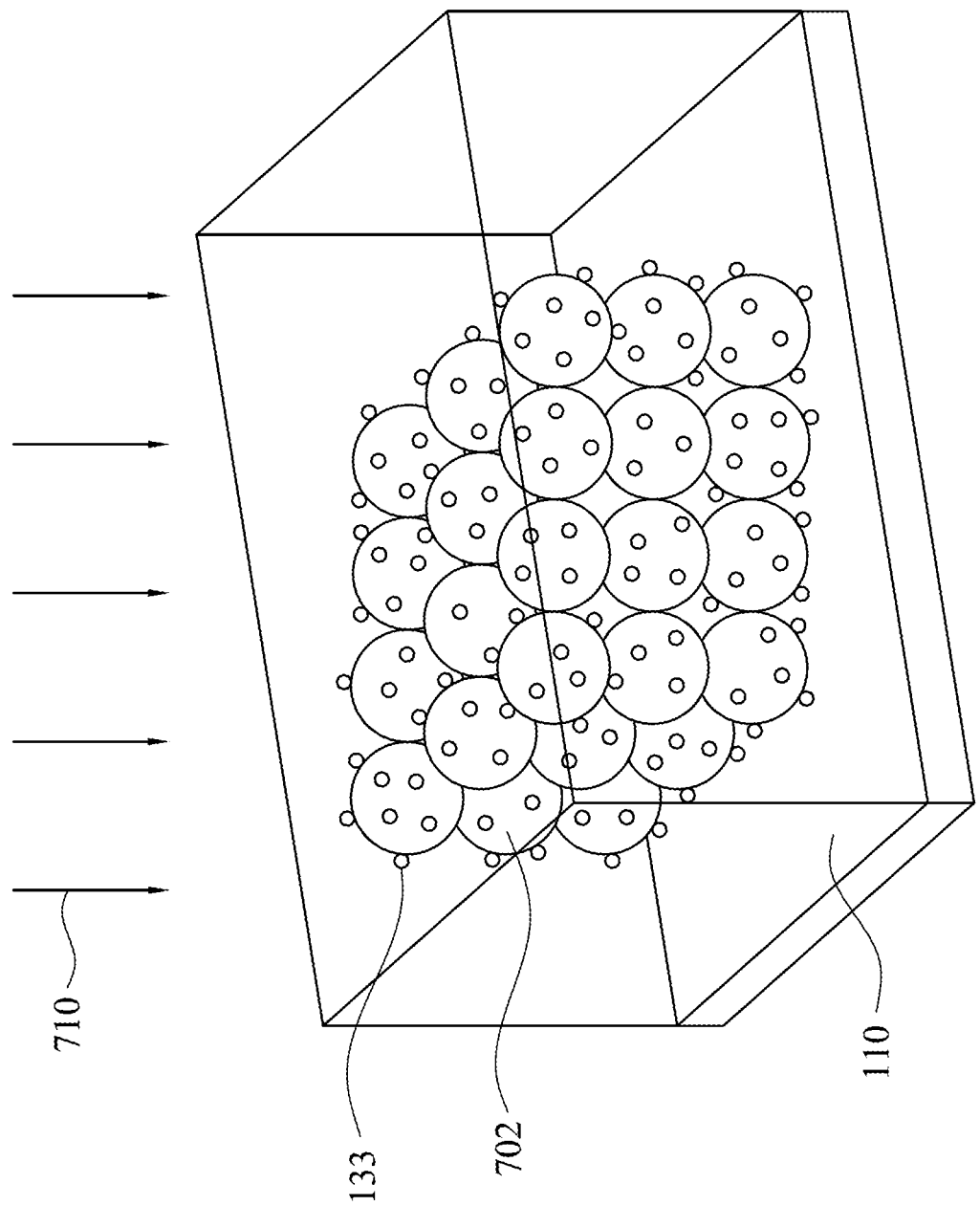

Next, as shown in FIG. 7B, a second polymer material layer 130' is formed on the face-centered cubic structure 700, such that the second polymer material layer 130' covers the face-centered cubic structure 700. The second polymer material layer 130' is formed by forming a polymer material on the face-centered cubic structure 700, followed by hardening the polymer material by exposing the polymer material to UV light. In some embodiments, the polymer material may further include a photoinitiator. Alternatively, the second polymer material layer 130' may be hardened by merely drying the polymer material on the face-centered cubic structure 700. In one example, the polymer material is PEGDA. Then, as shown in FIG. 7C, applying a silicon dioxide etchant (i.e. buffered oxide etch; BOE) 710 to the second polymer material layer 130' and the face-centered cubic structure 700, thereby removing the silicon dioxide nanobeads 702 to form the inverse opal photonic crystal structure 130A (FIG. 1C) of the second polymer layer 130. In other words, the inverse opal photonic crystal structure 130A is an inverted structure of the face-centered cubic structure 700. Because the gold nanoparticles 133 are not etched by the silicon dioxide etchant 710, the gold nanoparticles 133 are preserved and distributed on the wall 131S of the holes 131 of the inverse opal photonic crystal structure 130A after the silicon dioxide nanobeads 702 are removed, as shown in FIG. 1C.

Figure 7D:
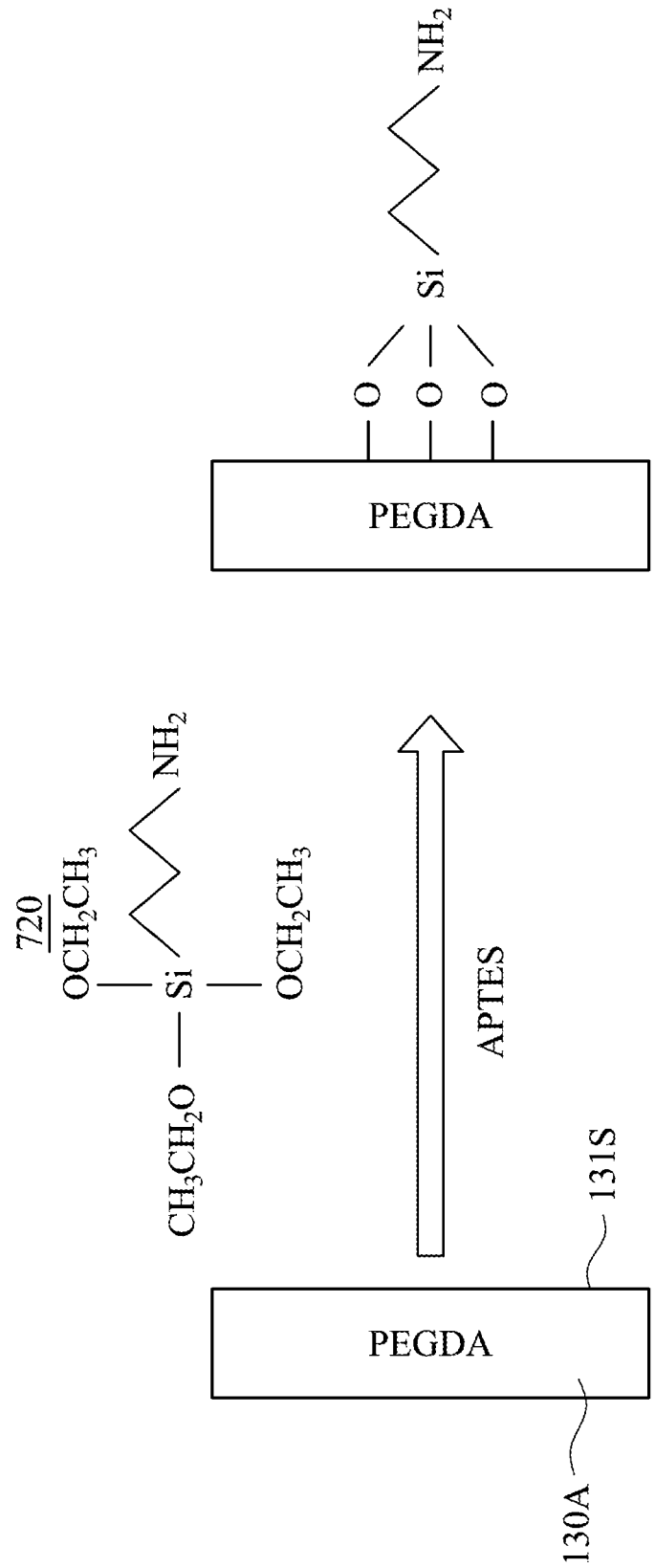
Figure 7E:
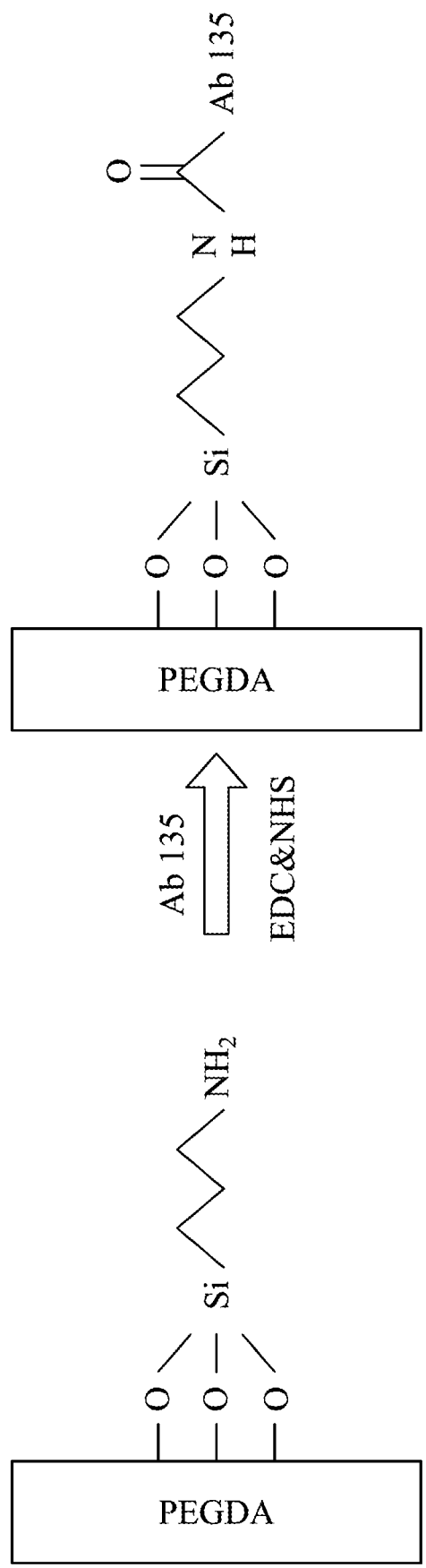

FIG. 7C and FIG. 7D merely show a portion of the inverse opal photonic crystal structure 130A and the wall 131S of its holes for simplification of figures. As shown in FIG. 7D, an amino alkylalkoxy silane compound 720 is bound to the wall 131S through a silicon-oxygen covalent bond. Then, as shown in FIG. 7E, an amino group of the amino alkylalkoxy silane compound 720 is bound to a hydroxyl group of the second antibody 135, thereby immobilizing the second antibody 135 on the wall 131S through an amide bond, so as to form the second polymer layer 130 shown in FIG. 1C. In one example, a reaction of 1-ethyl-3-(3-dimethylaminopropyl) carbodiimide (EDC) and N-hydroxysuccinimide (NHS) may be used to form a bond between the amino alkylalkoxy silane compound 720 and the second antibody 135. In one example, the amino alkylalkoxy silane compound 720 may be 3-aminopropyltriethoxysilane (APTES).

After the second polymer layer 130 is formed, a mixture of another polymer material and the composite antibodies 121 of FIG. 1B is filled into the first region 112, followed by hardening the polymer material by exposing the polymer material to the UV light, so as to form the first polymer layer 120. In some embodiments, the polymer material may further include a photoinitiator. Alternatively, the first polymer layer 120 may be hardened by merely drying the polymer material A material of the first polymer layer 120 may be same as or different from the material of the second polymer layer 130. For example, the first polymer layer 120 may be PEG. Preferably, the third polymer layer 140 of polymethyl methacrylate may be formed on the first polymer layer 120, as shown in FIG. 1A.

In the other embodiments, the first polymer layer may be formed in the first region prior to forming the second polymer layer in the second region. For example, in the biosensor 200, the first polymer layer 220 is formed in the first region 212, and then the second polymer layer 230 is formed in the second region 214 on the first polymer layer 220.

Figure 8:
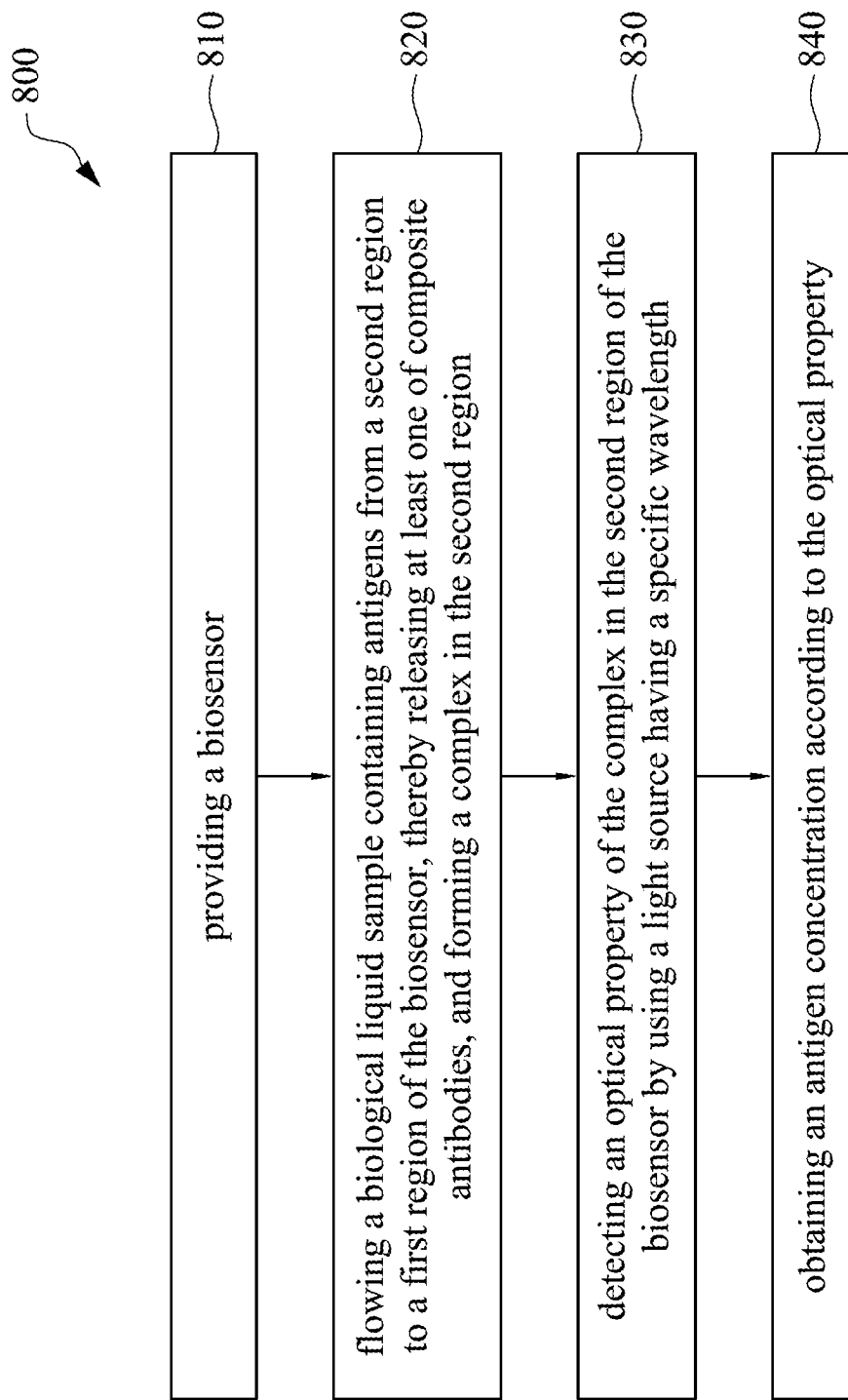
FIG. 8 is a schematic flow chart of a method of detecting an antigen concentration in accordance with one embodiment of the present invention.
Figure 9:
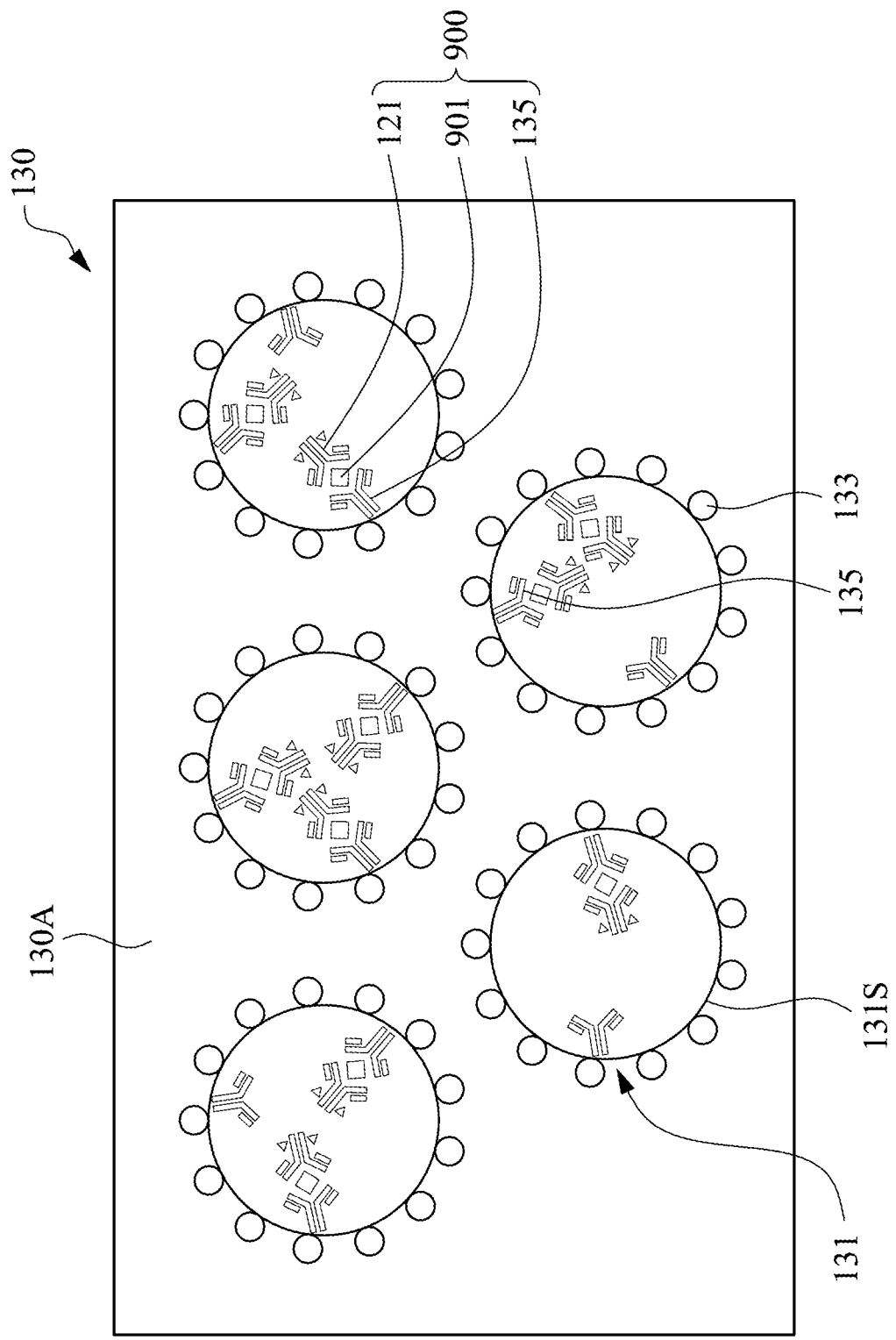
FIG. 9 is a schematic cross sectional view of a second polymer layer having a complex formed therein.

Another purpose of the present invention provides a method for detecting an antigen concentration, and the method may be performed by any biosensor described above. Details are explained in the following description by referring to FIG. 8 and FIG. 9. FIG. 8 illustrates a schematic flow chart of a method 800 of detecting an antigen concentration in accordance with one embodiment of the present invention. FIG. 9 illustrates a schematic cross sectional view of a second polymer layer having a complex formed therein. Although the second polymer layer 130 of the biosensor 100 is illustrated in FIG. 9, the second polymer layer of the biosensors 200, 300, 400, 500 or 600 may also be used.

As shown in FIG. 8 and FIG. 9, in a step 810, the biosensor 100 is provided, in which the substrate 110 of the biosensor 100 includes the first region 112 and the second region 114 connected to the first region 112. The second region 114 is located on one side of the first region 112. Next, in a step 820, a biological liquid sample including antigens 901 flow from the second region 114 of the biosensor 100 into the first region 112, thereby releasing the composite antibodies 121 of the first region 112. Specifically, the micropores of the first polymer layer 120 and the second polymer layer 130 are enlarged because the first polymer layer 120 and the second polymer layer 130 are swelled after absorbing the liquid, and thus at least one of the plural composite antibodies 121 may flow from the first region 112 into the second region 114. At least one of the composite antibodies 121 is reacted with the antigens 901 and at least one of the plural second antibodies 135 for a specific period of time, so as to form the complex 900 in the second region 130. In some embodiments, the biological liquid sample may be, for example, tears, urine, blood, or the like. In one embodiment, an antigen concentration in the biological liquid sample is at least 10 μg/ml. In one embodiment, when the contact lens of the biosensor 300, 400 or 500 is used, a specific antigen concentration in the tears secreted by a human eye is determined by directly wearing the contact lens and detecting the antigen in the tears that flowed over the first region and the second region. In one embodiment, the contact lens may be worn for 8 hours to continuously observe a variation in the concentration of the specific antigens 901 for a long-term examination. In one example, the antigens 901 may be lipocalin 1 (LCN1), the first antibody 125 (FIG. 1B) is a monoclonal antibody of LCN1, and the second antibody 135 may be a polyclonal antibody of LCN1.

Next, as shown in a step 830, an optical property of the complex in the second region is detected by using a light source having a specific wavelength. Specifically, the optical property may be, for example, a fluorescence intensity, a degree of red-shift or a visual color, when the labelling molecule 123 is the fluorescent molecule. In some embodiments, the specific wavelength is 200 nm to 700 nm. The light source may be, for example, a light source from a mobile phone or other light-emitting devices. In one example, the light source of the mobile phone is used with a fluorescent filter to obtain the specific wavelength.

Next, as shown in a step 840, the antigen concentration is obtained according to the optical property. In some embodiments, a mobile application program may be used to detect a change in the fluorescence intensity, thereby performing a quantitative analysis to obtain the antigen concentration. In other embodiments, the change in the fluorescence intensity may be detected by any other common fluorescence detecting instruments (e.g. a spectrometer) to obtain the antigen concentration. In further embodiments, the variation in the antigen concentration may be determined by a change in the visual color of the biosensor.

In some embodiments, compared to the biosensor without the photonic crystal structure, the fluorescence intensity of the biosensors 100, 200, 300, 400, 500 and 600 is increased by at least two times.

Figure 10:
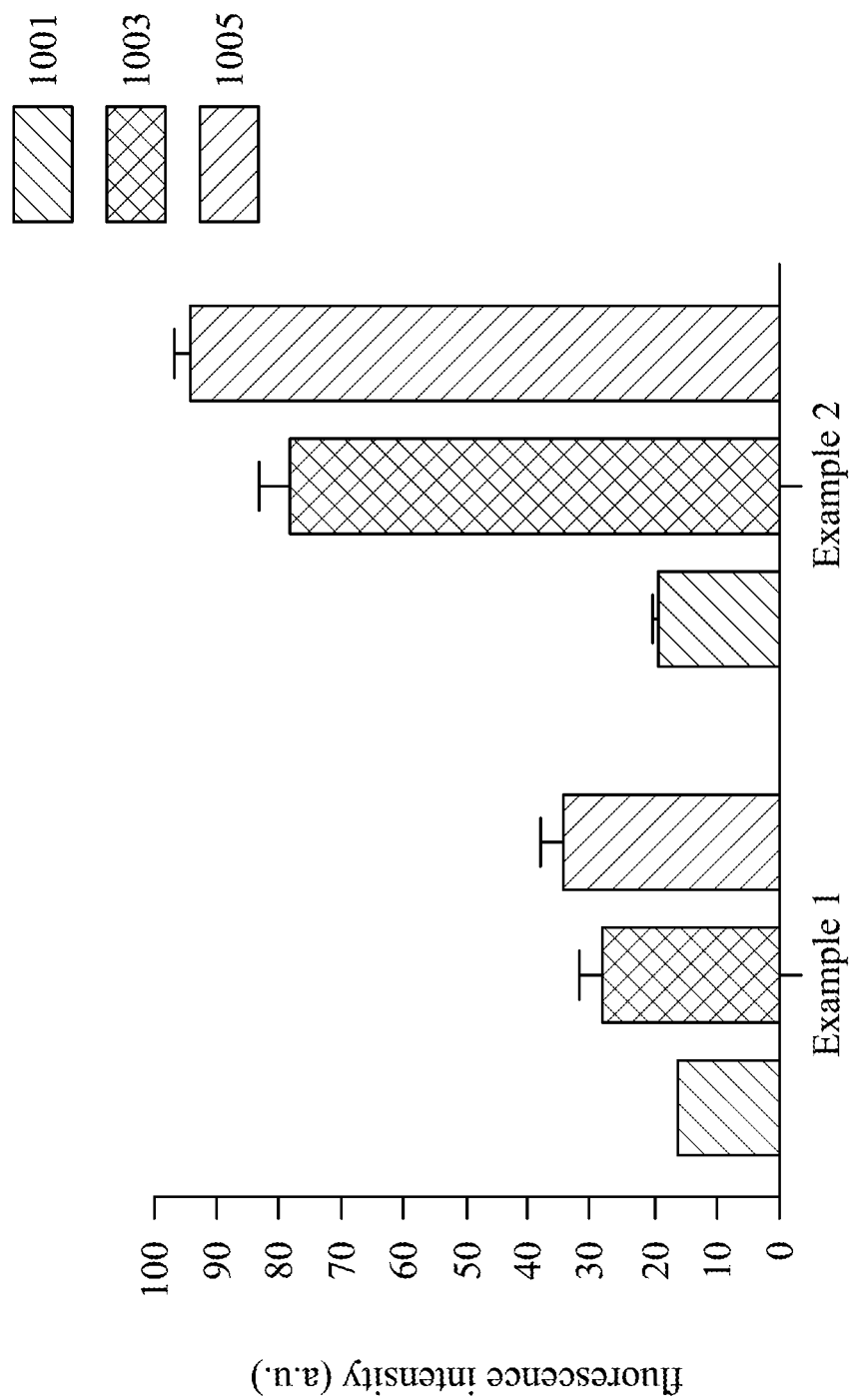
FIG. 10 is a bar chart of fluorescent intensities of Example 1 and Example 2 of the present invention.

Please refer to FIG. 10. FIG. 10 is a bar chart of fluorescent intensities of Example 1 and Example 2 of the present invention. In Example 1 and Example 2, a LCN1 polyclonal antibody connected to fluorescent molecules flows into a biosensor without the photonic crystal structure (bar 1001), a biosensor with the photonic crystal structure formed by 200 nm silicon dioxide (bar 1003), and a biosensor with the photonic crystal structure formed by 300 nm silicon dioxide (bar 1005), and the biosensors are examined to compare an effect of the photonic crystal structure on the fluorescence intensity. Alexa Fluor_488 is used as the fluorescent molecule in Example 1 and Example 2, in which a concentration of the polyclonal antibodies in Example 1 is 100 μg/ml, and a concentration of the polyclonal antibodies in Example 2 is 1 mg/ml.

According to FIG. 10, the photonic crystal structure can also efficiently improve the fluorescence intensity (e.g. two to three times), even when lower concentrations of the fluorescent molecule are used. A further improvement is particularly observed in the photonic crystal formed by 300 nm silicon dioxide. Moreover, when a higher concentration of the fluorescent molecule is used, the fluorescence intensity using the photonic crystal is significantly different from the fluorescence intensity without using the photonic crystal. In addition, according to the result of Example 1 and Example 2, when the biosensor lacks the photonic crystal structure, the fluorescence intensity cannot be improved in regardless of the increased concentration of the fluorescent molecule.

Figure 11:
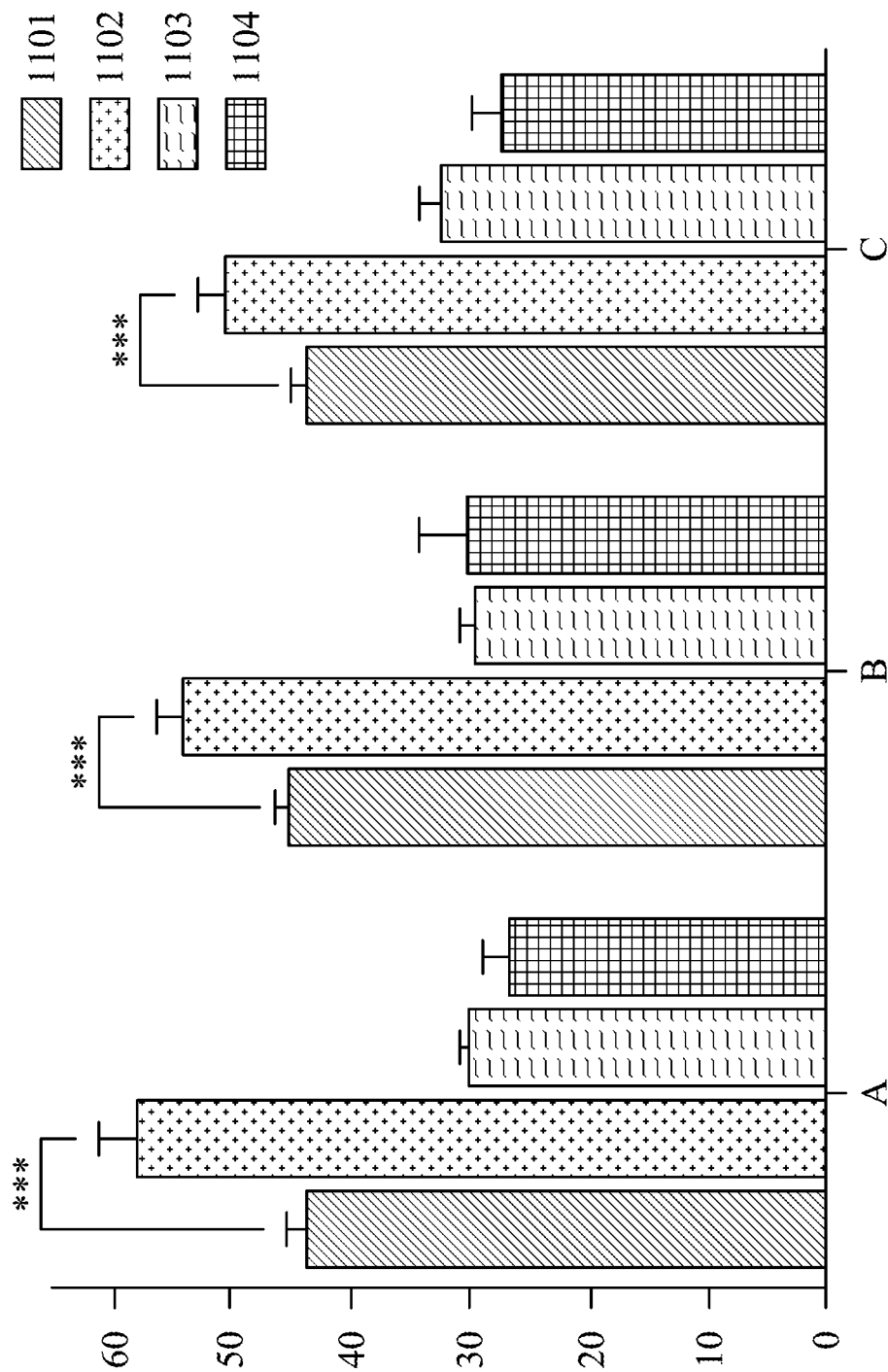
FIG. 11 is a bar chart of fluorescence intensities of Example 3 of the present invention.

Then, please refer to FIG. 11. FIG. 11 is a bar chart of fluorescence intensities of Example 3 of the present invention. In Example 3, a bar 1101 represents a fluorescence intensity of the biosensor of the present invention prior to a reaction, and a bar 1102 represents a fluorescence intensity of the biosensor of the bar 1101 after an immune-sandwich structure is formed. A bar 1103 represents a fluorescence intensity of a biosensor without the photonic crystal structure prior to a reaction, and a bar 1104 represents a fluorescence intensity of the biosensor of the bar 1103 after an immune-sandwich structure is formed. The two types of the biosensor are respectively formed by using 0.1 mg/ml of fluorescent molecules connected to LCN1 polyantibodies (poly: fluorescent molecule is 2:1), and 0.1 mg/ml of LCN1 monoantibodies. Groups A, B and C in Example 3 are performed by using liquid samples respectively containing 0.1 mg/ml, 0.05 mg/ml, and 0.01 mg/ml of LCN1, and the liquid samples are reacted with the liquid samples for 8 hours, thereby forming the immuno-sandwich structure in the biosensors. As shown in FIG. 11, the fluorescence intensity is significantly improved in the biosensor with the photonic crystal structure. The intensity of the group A increases by 33% (i.e. a difference between the bar 1101 and the bar 1102), the intensity of the group B increases by 16%, and the intensity of the group C increases by 12%.

Figure 12A:
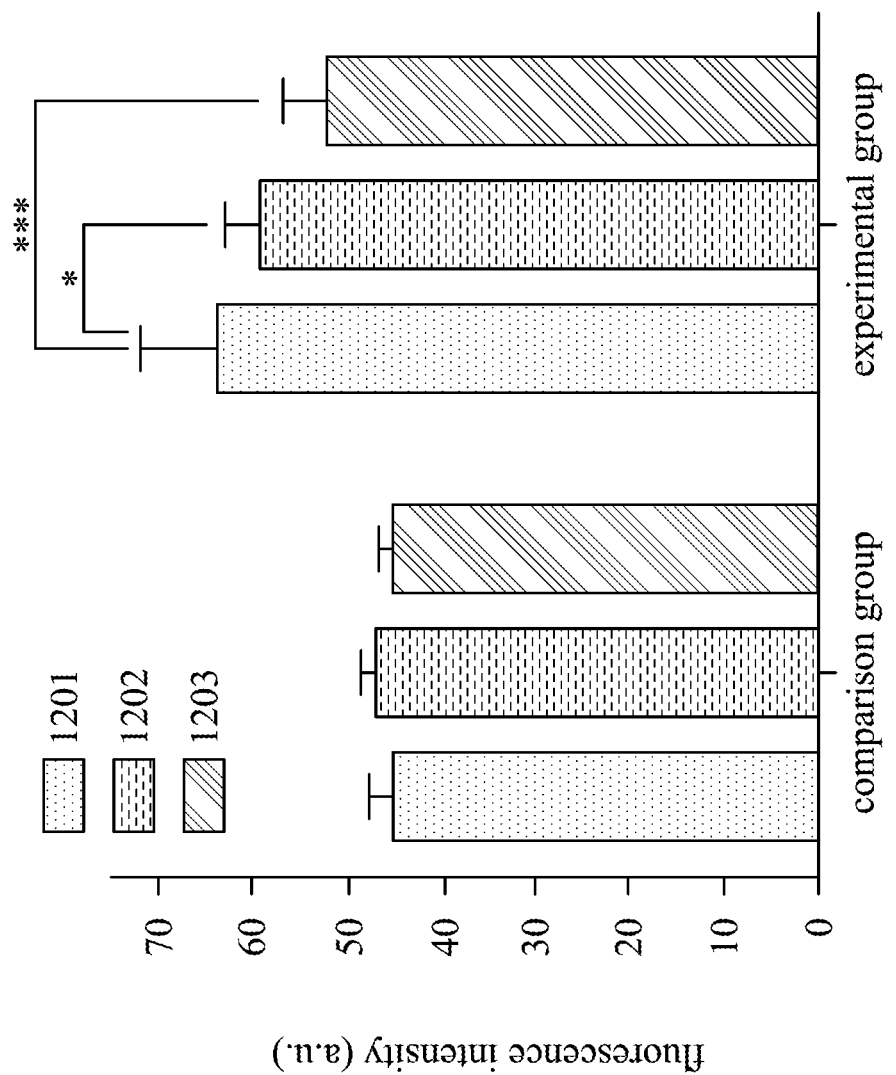
FIG. 12A and FIG. 12B are bar charts of fluorescence intensities and a fluorescence enhancement factor of Example 4 of the present invention.
Figure 12B:
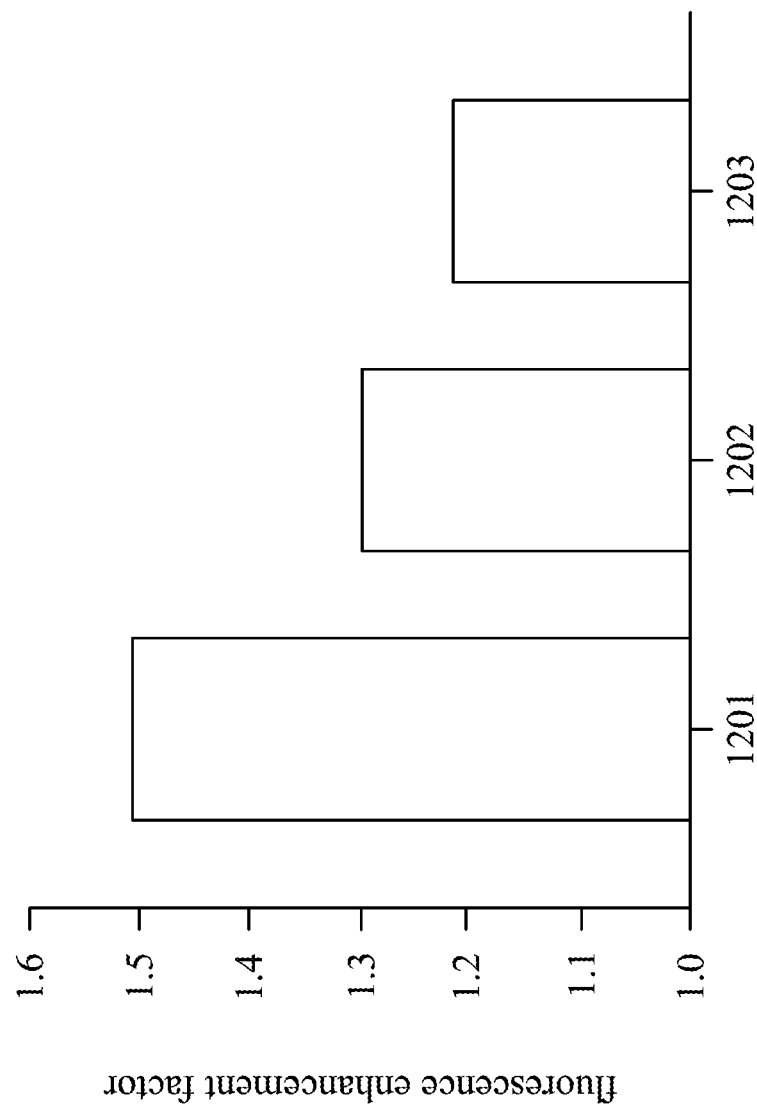

Next, please refer to FIG. 12A and FIG. 12B. FIG. 12A and FIG. 12B are bar charts of fluorescence intensity and fluorescence enhancement factor of Example 4 of the present invention. In Example 4, the fluorescence intensities of biosensors of a comparison group are measured prior to the addition of the liquid samples, and the fluorescence intensities of the biosensors of an experimental group are detected after the addition of the liquid samples into the biosensors for 3 hours. A bar 1201 represents a fluorescence intensity of the biosensor of the present invention. A bar 1202 represents a fluorescence intensity of the biosensor which the liquid sample without LCN 1 flows therein. A bar 1203 represents a fluorescence intensity of the biosensor without antibodies immobilized in the photonic crystal. The biosensors of the bar 1201, bar 1202 and bar 1203 are formed by similar conditions to Example 3, and the liquid samples that flowed into the biosensors of the bar 1201 and bar 1203 include 0.1 mg/ml LCN1. As shown in FIG. 12A, the fluorescence intensity of the biosensor of the present invention (bar 1201) is significantly different from the fluorescence intensities of the bar 1202 and bar 1203, in which the fluorescence intensities of the bar 1202 and bar 1203 result from non-specific binding. Furthermore, as shown in FIG. 12B, the fluorescence enhancement factor (i.e. a ratio of the experimental group to the comparison group) of the biosensor of the present invention is greater than that of the other biosensors.

Through forming the immune-sandwich structure and the surface plasma resonance of the gold nanoparticles in the inverse opal photonic crystal structure to increase the refraction and the reflection of light, a detecting property of the biosensor of the present invention is improved (for example, the fluorescence intensity and/or the degree of red-shift is increased). Therefore, antigens at low concentrations may be detected by the biosensor of the present invention, and a variation in the antigen concentration may be determined by a change of the visual color of the biosensor. Uniform sampling and a long-term examination of the variation in the antigen concentration are realized by the biosensor.

Although the present invention has been described in considerable detail with reference to certain embodiments thereof, the spirit and scope of the appended claims should not be limited to the description of the embodiments contained herein. It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims.

What is claimed is:

1. A biosensor, comprising:
   a substrate, wherein the substrate comprises a first region and a second region adjoined to the first region, the second region is located on one side of the first region, a center of the substrate is concentrically surrounded by the first region and the second region in order from outside to inside, a bottom of the first region has a recessed cross section having a first depth, a bottom of the second region has a recessed cross section having an asymmetric U-shape and a second depth, the second depth is greater than the first depth, and a slope of a side wall of the recessed cross section of the second region near the center is greater than a slope of another other side wall of the recessed cross section of the second region near the first region;
   a first polymer layer, disposed in the first region, wherein a plurality of composite antibodies are distributed in the first polymer layer, and each of the composite antibodies comprises a labelling molecule and a first antibody connected to the labelling molecule; and
   a second polymer layer, disposed in the second region, wherein the second polymer layer has an inverse opal photonic crystal structure, the inverse opal photonic crystal structure comprises a plurality of holes, a plurality of gold nanoparticles and a plurality of second antibodies are disposed on a wall of each of the holes, and the first antibody and the second antibodies recognize the same antigen.

2. The biosensor of claim 1, wherein the second region is located over the first region.

3. The biosensor of claim 1, wherein the inverse opal photonic crystal structure is an inverted structure of a face-centered cubic structure of nanobeads, each of the nanobeads has a particle size in a range from 100 nm to 1000 nm, and the gold nanoparticles are distributed on a surface of each of the nanobeads.

4. The biosensor of claim 1, wherein the labelling molecule comprises a fluorescent molecule, and a particle size of each of the gold nanoparticles is in a range from 5 nm to 80 nm.

5. The biosensor of claim 1, further comprising a third polymer layer over the first polymer layer.

6. The biosensor of claim 1, wherein the biosensor is a contact lens, the center of the substrate is an optical zone of the contact lens, the first region and the second region are located in a non-optical zone of the contact lens, at least the second polymer layer is exposed on one surface of the contact lens, and opposes a surface that is in direct contact with an eye.

7. A method of detecting an antigen concentration, comprising:
   providing a biosensor described in claim 1, wherein a substrate of the biosensor comprises a first region and a second region connected to the first region, and the second region is located on one side of the first region;
   flowing a biological liquid sample containing an antigen from the second region to the first region of the biosensor, thereby releasing at least one of a plurality of composite antibodies comprising a first antibody and a labelling molecule, and reacting the at least one of the composite antibodies for a period of time with the antigen and at least one of a plurality of second antibodies to form a complex in the second region;
   detecting an optical property of the complex in the second region of the biosensor by using a light source having a specific wavelength, wherein the optical property comprises a fluorescence intensity or a visual color; and
   obtaining an antigen concentration according to the optical property.

8. The method of claim 7, wherein the specific wavelength is in a range from 200 nm to 700 nm, and the fluorescence intensity is increased by at least two times based on an inverse opal photonic crystal structure in the second region.

* * * * *